US010718758B2

(12) United States Patent
Bruce et al.

(10) Patent No.: US 10,718,758 B2
(45) Date of Patent: *Jul. 21, 2020

(54) BIOSENSOR FOR OPTICAL DETECTION OF NUCLEOTIDE SEQUENCE

(71) Applicant: INTERNATIONAL BUSINESS MACHINES CORPORATION, Armonk, NY (US)

(72) Inventors: Robert L. Bruce, White Plains, NY (US); Payel Das, Yorktown Heights, NY (US); HsinYu Tsai, White Plains, NY (US); Sufi Zafar, Briarcliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 264 days.

This patent is subject to a terminal disclaimer.

(21) Appl. No.: 15/172,737

(22) Filed: Jun. 3, 2016

(65) Prior Publication Data

US 2017/0350820 A1 Dec. 7, 2017

(51) Int. Cl.
*G01N 27/00* (2006.01)
*G01N 33/52* (2006.01)
*G01N 33/543* (2006.01)

(52) U.S. Cl.
CPC ....... *G01N 33/525* (2013.01); *G01N 33/5438* (2013.01)

(58) Field of Classification Search
CPC .................................. B82Y 40/00; B82Y 5/00
USPC ................................................. 977/888, 890
See application file for complete search history.

(56) References Cited

U.S. PATENT DOCUMENTS

| 5,821,060 | A | 10/1998 | Arlinghaus et al. | |
|---|---|---|---|---|
| 6,342,359 | B1 | 1/2002 | Lee et al. | |
| 7,101,671 | B2 | 9/2006 | Gao | |
| 2003/0013203 | A1* | 1/2003 | Jedrzejewski | B01J 19/0046 436/102 |
| 2004/0028875 | A1* | 2/2004 | Van Rijn | A61L 27/50 428/98 |
| 2004/0101845 | A1 | 5/2004 | Collins et al. | |
| 2004/0101846 | A1 | 5/2004 | Collins et al. | |
| 2005/0095596 | A1 | 5/2005 | Leproust et al. | |
| 2007/0099198 | A1 | 5/2007 | Hassibi et al. | |
| 2008/0027654 | A1 | 1/2008 | Nelson et al. | |
| 2010/0234235 | A1 | 9/2010 | Kaplan | |
| 2016/0281149 | A1 | 9/2016 | Hassibi et al. | |

OTHER PUBLICATIONS

Mir et al., Abstract for "Sequence variation in genes and genomic DNA: methods for large-scale analysis", Annual Review of Genomics and Human Genetics (Annu Rev Genom Hum G), vol. 1, No. 1, pp. 329-360, Feb. 2000.

Homola, "Surface Plasmon Resonance Sensors for Detection of Chemical and Biological Species", Chem. Rev. 2008, vol. 108, pp. 462-493.
Liepold et al., "Electrically detected displacement assay (EDDA): a practical approach to nucleic acid testing in clinical or medical diagnosis", Anal Bioanal Chem (2008), vol. 391: pp. 1759-1772.
Hall, Book: "Biosensors", Prentice Hall advanced reference series: Engineering Against the Clock Biotechnology series, Prentice Hall 1991, 351 pages.
Schena, Overview of "Microarray Analysis", New York: Wiley-Liss, John Wiley & Sons, Inc., 2003, 654 pages, Clinical Chemistry, vol. 49, No. 6, 2003, pp. 1031-1033.
Edited by: Kazuaki Suzuki, Bruce W. Smith, "Microlithography", Science and Technology, Second Edition, CRC Press, 2007, Sidewall Image Transfer, pp. 93-94.
IBM: List of IBM Patents or Patent Applications Treated as Related (Appendix P), Jul. 17, 2019, pp. 1-2.
Pending U.S. Appl. No. 16/454,203, filed Jun. 27, 2019, entitled: Reduction of Surface Nucleotide Hybridization by Optimizing a Biosensor Sensing Surface Area, 31 pages.
Anne et al., "Dynamics of Electron Transport by Elastic Bending of Short DNA Duplexes. Experimental Study and Quantitative Modeling of the Cyclic Voltammetric Behavior of 3'-Ferrocenyl DNA End-Grafted on Gold," J. Am. Chem. Soc. 2006, Copyright 2006 American Chemical Society, pp. 542-557.
Kaiser et al., "Conformations of End-Tethered DNA Molecules on Gold Surfaces: Influences of Applied Electric Potential, Electrolyte Screening, and Temperature," J. Am. Chem. Soc. 2010, Copyright 2010 American Chemical Society, pp. 7935-7945.
Li et al., "Separation of DNA with Different Configurations on Flat and Nanopatterned Surfaces," Analytical Chemistry, vol. 78, No. 14, Jul. 15, 2006. Copyright 2006 American Chemical Society, pp. 4743-4751.
Peterson et al., "The effect of surface probe density on DNA hybridization," Nucleic Acids Research, 2001, vol. 29, No. 24, Copyright 2001 Oxford University Press, pp. 5163-5168.
Petrovykh et al., "Quantitative Analysis and Characterization of DNA Immobilized on Gold," J. Am. Chem. Soc., 2003, Copyright 2003 American Chemical Society, pp. 5219-5226.
Relogio et al., "Optimization of oligonucleotide-based DNA microarrays," Nucleic Acids Research, 2002, vol. 30, No. 11, Copyright 2002 Oxford University Press, pp. 1-10.
Sakata et al., "Potential Behavior of Bio-chemically Modified Gold Electrode for Extended Gate Field Effect Transistor," National Institute for Materials Science, Tsukuba, Ibaraki, Japan, Japanese Journal of Applied Physics (Impact Factor: 1.13), DOI: 10.1143/JJAP.44.2860, pp. 1-4.

(Continued)

*Primary Examiner* — Natalia Levkovich
(74) *Attorney, Agent, or Firm* — Reza Sarbakhsh

(57) ABSTRACT

The present invention relates generally to the field of microelectronics, and more particularly to a structure and method of forming a biosensor having a nucleotide attracting surface tailored to reduce false detection of nucleotides and enabling optical detection of nucleotides. The biosensor may include an analyte-affinity layer on an upper surface of a dielectric layer. The analyte-affinity layer may include a plurality of cylindrical gold portions with dimensions tailored for a target analyte. A distance between adjacent portions of the plurality of portions may range from approximately 50% of a length of a target analyte to approximately 300% of a length of a target analyte. The plurality of portions of the analyte-affinity layer have an upper surface with a diameter ranging from approximately 3 nm to approximately 20 nm.

17 Claims, 15 Drawing Sheets

(56) References Cited

OTHER PUBLICATIONS

Zhou et al., "Use of Atomic Force Microscopy for Making Addresses in DNA Coatings," Langmuir 2002 Copyright 2002 American Chemical Society, Published on Web Sep. 26, 2002, pp. 8278-8281.
Ruiz et al., "Density Multiplication and Improved Lithography by Directed Block Copolymer Assembly," Science, vol. 21, Aug. 15, 2008, pp. 936-939.
Cheng et al., "Pattern Registration Between Spherical Block-Copolymer Domains and Topographical Templates," Adv. Mater., 2006, vol. 18, Copyright 2006 WILEY-VCH GmbH & Co. KGaA, Weinheim, pp. 597-601.
Cheng et al., "Templated Self-Assembly of Block Copolymers: Effect of Substrate Topography," Adv. Mater., 2003, vol. 15, No. 19, Oct. 2, 2003, Copyright 2003 WILEY-VCH GmbH & Co. KGaA, Weinheim, pp. 1599-1602.
Das et al., "Mechanistic Influence of Nanometer Length-Scale Surface Chemistry on DNA Hybridization," ACS NANO, vol. 9, No. 7, Jun. 8, 2015, pp. 7466-7478, Grace Period Disclosure.
Chen et al., "Ionic strength-dependent persistence lengths of single-stranded RNA and DNA," PNAS, vol. 109, No. 3, Jan. 17, 2012, pp. 799-804.
Rechendorff et al., "Persistence length and scaling properties of single-stranded DNA adsorbed of modified graphite," The Journal of Chemical Physics, 131, 095103, 2009, Copyright 2009 American Institute of Physics, pp. 1-6.
Koltai et al., "Specificity of DNA microarray hybridization: characterization, effectors and approaches for data correction," Nucleic Acids Res., Apr. 2008, 36(7), Copyright 2008 The Author(s), pp. 2395-2405.
Fiche et al., "Temperature Effects on DNA Chip Experiments from Surface Plasmon Resonance Imaging: Isotherms and Melting Curves," Biophys J., Feb. 1, 2007; 92(3), Copyright 2007, Biophysical Society, pp. 935-946.
Chen et al., "Kinetics and thermodynamics of DNA hybridization on gold nanoparticles," Nucleic Acids Res., Jun. 2009; 37(11), Copyright 2009 The Author9(s), pp. 3756-3765.
Draghici et al., "Reliability and reproducibility issues in DNA microarray measurements," Trends Genet, Feb. 2006; 22(2), pp. 101-109.
Levicky et al., "Physicochemical perspectives on DNA microarray and biosensor technologies," TRENDS in Biotechnology, vol. 23, No. 3, Mar. 2005, Copyright 2005 Elsevier Ltd., pp. 143-149.
Chan et al., "The Biophysics of DNA Hybridization with Immobilized Oligonucleolide Probes," Biophysical Journal, vol. 69, Dec. 1995, Copyright 1995 by the Biophysical Society, pp. 2243-2255.
Dorvel et al., "Silicon Nanowires with High-k Hafnium Oxide Dielectrics for Sensitive Detection of Small Nucleic Acid Oligomers," HHS Public Access, Author manuscript, Published online Jun. 22, 2012, doi: 10.1021/nn301495k, http://www.ncbi.nlm.nih.gov/pmc/articles/PMC3412126/, Printed on Apr. 11, 2016, pp. 1-18.
Vora et al., "Directed Self-assembly of Topcoat-free, Integration-friendly High-X Block Copolymers," Journal of Photopolymer Science and Technology, vol. 27, No. 3 (2014), Copyright 2014PST, pp. 419-424.
Josephs et al., "Nanoscale Spatial Distribution of Thiolated DNA on Model Nucleic Acid Sensor Surfaces," ACS NANO, vol 7., No. 4, Jospehs and Ye, Copyright 2013 American Chemical Society pp. 3653-3660.
Josephs et al., "Electric-Field Dependent Conformations of Single DNA Molecules on a Model Biosensor Surface," Nano Lett., 2012, Published: Sep. 10, 2012, Copyright 2012 American Chemical Society, pp. 5255-5261.
IBM: List of IBM Patents or Patent Applicatlons Treated as Related (Appendix P), Jun. 6, 2016, pp. 1-2.
Bruce et al., Pending U.S. Appl. No. 15/172,759, filed Jun. 3, 2016, titled "Biosensor for Electrical Detection of a Nucleotide Sequence,", pp. 1-46.
Bruce et al., Pending U.S. Appl. No. 15/172,801, filed Jun. 3, 2016, titled "Reduction of Surface Nucleotide Hybridization by Optimizing a Biosensor Sensing Surface Area,", pp. 1-31.

* cited by examiner

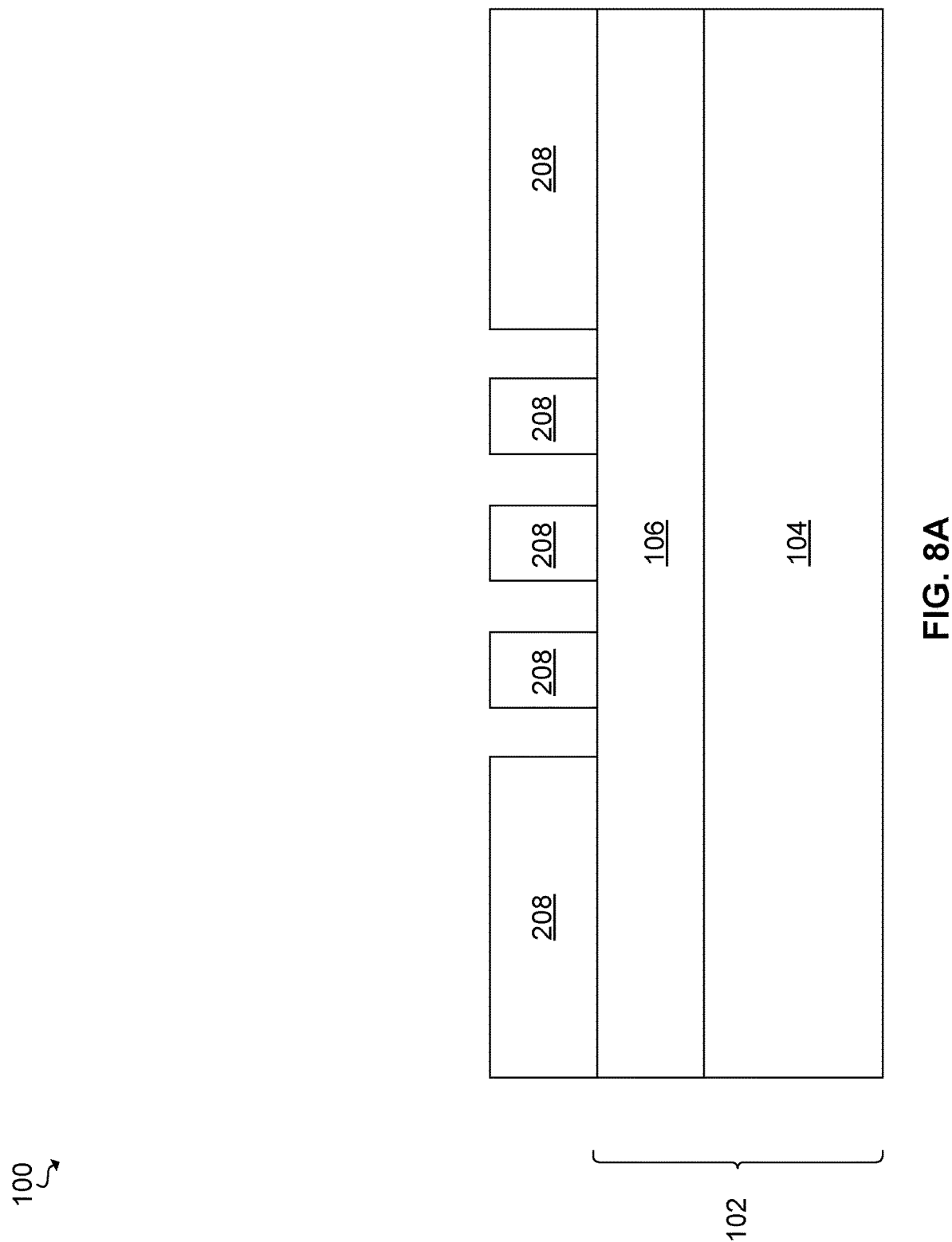

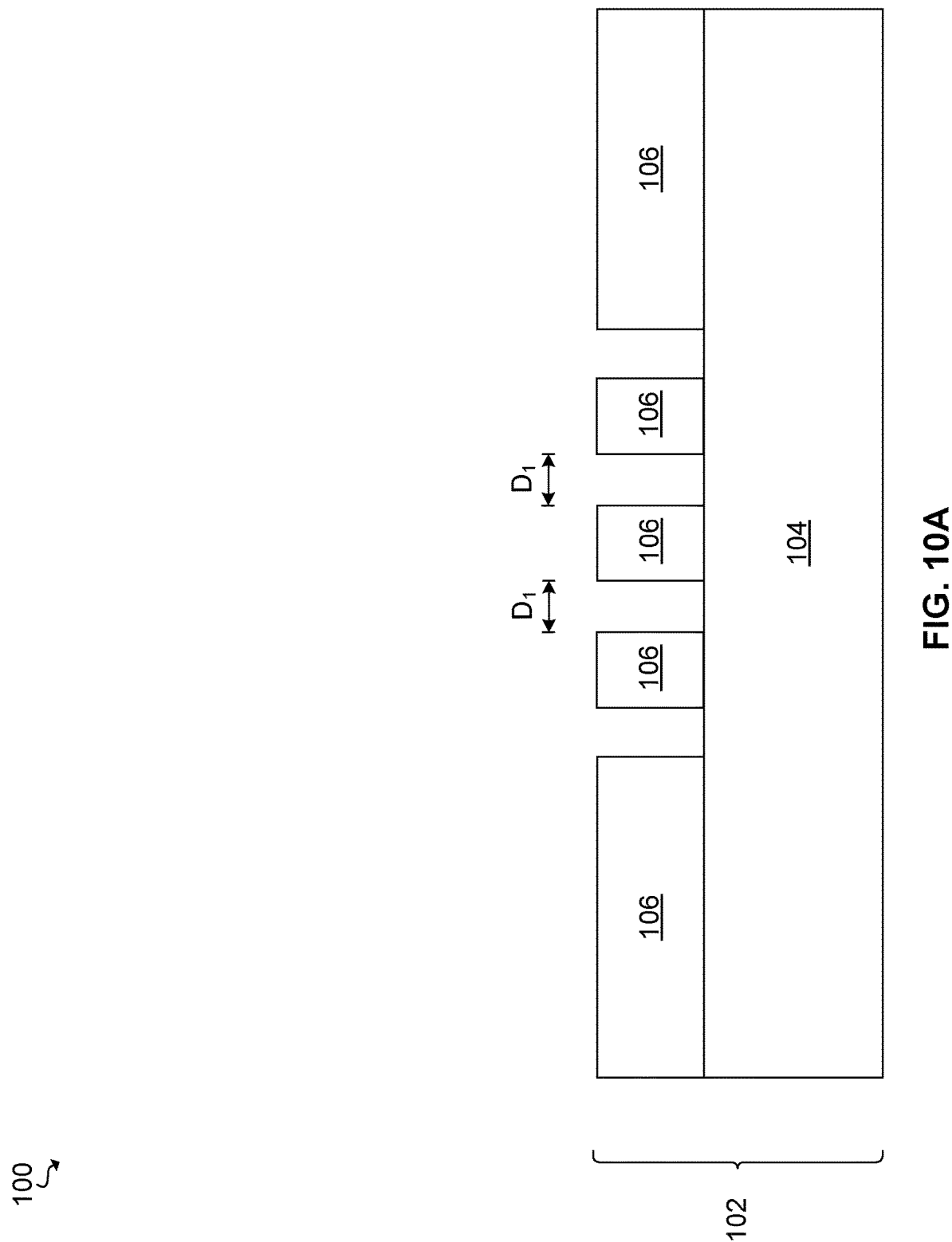

BIOSENSOR FOR OPTICAL DETECTION OF NUCLEOTIDE SEQUENCE

STATEMENT REGARDING PRIOR DISCLOSURE BY THE INVENTOR OR A JOINT INVENTOR

Aspects of the present invention have been disclosed in a publication made available to the public on Jun. 8, 2015. Payel Das & Sufi Zafar, *Mechanistic Influence of Nanometer Length-Scale Surface Chemistry on DNA Hybridization*, 7466-7478 (Jun. 8, 2015). The following disclosure is submitted under 35 U.S.C. § 102(b)(1)(A).

BACKGROUND

The present invention relates generally to the field of microelectronics, and more particularly to a structure and method of forming a biosensor having a nucleotide attracting surface tailored to reduce false detection of nucleotides and enabling optical detection of nucleotides.

Affinity-based biosensors may be used to identify and measure one or more analytes (e.g., proteins, nucleotides, etc.) in a sample. Selective interactions between an analyte and a surface of a biosensor may be exploited to attract a particular analyte to the surface of the biosensor. Affinity-based biosensors may be used in parallel (e.g., as in microarrays) to detect a large number of analytes at once.

SUMMARY

Embodiments of the present invention disclose a method of forming a biosensor having a nucleotide attracting surface tailored to reduce false detection of nucleotides. The method may include forming a second dielectric layer on an upper surface of a structure. The structure may include an analyte-affinity layer on a first dielectric layer. The method may include forming a photoresist layer on an upper surface of a second dielectric layer. The method may include removing a portion of the photoresist layer. Removing the portion of the photoresist layer may expose a portion of the upper surface of the second dielectric layer. The method may include forming a polymer layer on the exposed portion of the upper surface of the second dielectric layer. The method may include transforming the polymer layer into a first copolymer within a second copolymer. The method may include removing a first portion of the second copolymer adjacent to the first copolymer where a second portion of the second copolymer remains below the first copolymer. The method may include removing a third portion of the second dielectric layer below the first portion of the second copolymer down to an upper surface of the analyte-affinity layer where a fourth portion of the second dielectric layer remains below the first copolymer. The method may include removing the first copolymer, the second copolymer, and the photoresist layer. The method may include removing a fifth portion of the analyte-affinity layer adjacent to the fourth portion of second dielectric layer where a sixth portion of the analyte-affinity layer remains below the fourth portion of the second dielectric layer. The method may include removing the second dielectric layer.

Embodiments of the present invention disclose a method of forming a biosensor having a nucleotide attracting surface tailored to reduce false detection of nucleotides. The method may include forming a second dielectric layer on an upper surface of a structure. The structure may include an analyte-affinity layer on a first dielectric layer. The method may include forming a photoresist layer on an upper surface of a second dielectric layer. The method may include removing a portion of the photoresist layer where the removing the portion of the photoresist layer exposes a portion of the upper surface of the second dielectric layer. The method may include forming a polymer layer on the exposed portion of the upper surface of the second dielectric layer. The method may include transforming the polymer layer into a plurality of first copolymers within a second copolymer. The method may include removing a first portion of the second copolymer adjacent to the plurality of first copolymers where a plurality of second portions of the second copolymer remain below the plurality of first copolymers. The method may include removing a third portion of the second dielectric layer below the first portion of the second copolymer down to an upper surface of the analyte-affinity layer where a plurality of fourth portions of the second dielectric layer remain below the plurality of first copolymers. The method may include removing the plurality of first copolymers, the second copolymer, and the photoresist layer. The method may include removing a fifth portion of the analyte-affinity layer adjacent to the plurality of fourth portions of second dielectric layer where a plurality of sixth portions of the analyte-affinity layer remain below the plurality of fourth portions of the second dielectric layer. The method may include removing the second dielectric layer.

Embodiments of the present invention disclose a structure having a nucleotide attracting surface tailored to reduce false detection of nucleotides. The structure may include a plurality of portions of an analyte-affinity layer on an upper surface of a dielectric layer. The plurality of portions may have a cylindrical shape. The analyte-affinity layer may include gold. The dielectric layer may include silicon oxide. A distance between adjacent portions of the plurality of portions may range from approximately 50% of a length of a target analyte to approximately 300% of a length of a target analyte.

BRIEF DESCRIPTION OF THE SEVERAL VIEWS OF THE DRAWINGS

The following detailed description, given by way of example and not intended to limit the invention solely thereto, will best be appreciated in conjunction with the accompanying drawings.

FIGS. 8A-8B are a cross-section view and an isometric view, respectively, of removing the first copolymer, the second copolymer, and the photoresist layer, in accordance with an embodiment of the present invention.

FIGS. 10A-10B are a cross-section view and an isometric view, respectively, of removing the second dielectric layer, in accordance with an embodiment of the present invention.

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Figure 1:
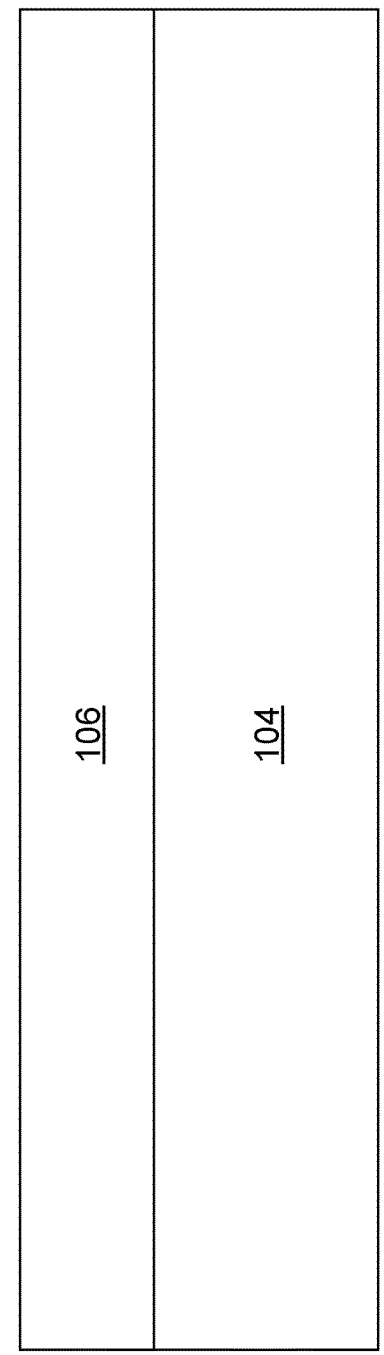
FIG. 1 is a cross-section view of a structure having a first dielectric layer and an analyte-affinity layer, in accordance with an embodiment of the present invention.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art.

For purposes of the description hereinafter, the terms "upper", "lower", "right", "left", "vertical", "horizontal", "top", "bottom", and derivatives thereof shall relate to the disclosed structures and methods, as oriented in the drawing figures. It will be understood that when an element such as a layer, region, or substrate is referred to as being "on", "over", "beneath", "below", or "under" another element, it may be present on or below the other element or intervening elements may also be present. In contrast, when an element is referred to as being "directly on", "directly over", "directly beneath", "directly below", or "directly contacting" another element, there may be no intervening elements present. Furthermore, the terminology used herein is for the purpose of describing particular embodiments only and is not intended to be limiting of the invention. As used herein, the singular forms "a," "an," and "the" are intended to include the plural forms as well, unless the context clearly indicates otherwise.

In the interest of not obscuring the presentation of embodiments of the present invention, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is rather focused on the distinctive features or elements of various embodiments of the present invention.

The present invention relates generally to the field of microelectronics, and more particularly to a structure and method of forming a biosensor having a nucleotide attracting surface tailored to reduce false detection of nucleotides and enabling optical and electrical detection of nucleotides. Affinity-based biosensors may be used to identify and measure one or more analytes (e.g., proteins, nucleotides, etc.) in a sample. Selective interactions between an analyte and a surface of a biosensor may be exploited to attract a particular analyte to the surface of the biosensor. Affinity-based biosensors may be used in parallel (e.g., as in microarrays) to detect a large number of analytes at once.

Conventional affinity-based biosensor structures (e.g. microarrays) may result in a number of false positives and false negatives (e.g., incorrectly identifying a presence or absence of an analyte). In an embodiment, an analyte (e.g., a nucleotide sequence) in contact with a surface of biosensor may partially interact with a complimentary analyte (e.g., a complementary nucleotide sequence) or another analyte and result in a false positive. For example, microarrays may result in approximately 75% accuracy. An affinity-based biosensor may include a gold surface. Gold may be used to study the interactions governing surface hybridization due to its useful properties as a model substrate. However, hybridization on gold is affected by nonspecific adsorption of the exposed bases of small strand DNA or ss-DNA. Nonspecific DNA gold interaction is found to be base-dependent, following the order A>G>C>T. Typical probe sequences (nucleotides) at low surface densities exhibit hybridization efficiency of greater than 60% that is lower than what is observed in solution. A planar gold surface has been reported to significantly slow down and lower free energy of hybridization. Studies also suggested incomplete hybridization on gold. Due to typical probe sequences non-specific interactions with gold, the use of gold to increase the sensitivity and accuracy of probe-gold interactions is not an obvious solution.

Embodiments of the present invention provide a structure and method for forming a biosensor with a nucleotide-attracting surface having dimensions tailored to a nucleotide to reduce false positive and false negative readings. By including an attractive surface having dimensions tailored for a target analyte, a biosensor may reduce partial interactions between the probe analyte (e.g., a nucleotide sequence) and a target analyte (e.g., a complementary nucleotide sequence). For example, a target nucleotide sequence may have a known length and composition. An attractive surface may be included such that partial interactions between the probe-target pair may not stabilize on the attractive surface. Therefore, the attractive surface may only allow fully complementary interaction between a single nucleotide pair. A first attractive surface and a second attractive surface may be separated by a distance based on the known length of the target nucleotide pair. For example, a first gold surface of an analyte-affinity layer may be separated from a second gold surface by a distance greater than a length of a target nucleotide pair. By limiting dimensions of the attractive surface (e.g., an upper surface of an analyte-affinity layer) such that only a single nucleotide pair may fit on the attractive surface, interactions with other nucleotide pairs may be limited and hybridization of the nucleotide pair may be improved. By separating attractive surfaces by a distance greater than a length of a target nucleotide pair, interactions between nucleotide pairs may be reduced. A method of forming a biosensor with an attractive surface tailored to reduce false readings is described below with reference to FIGS. 1-10B.

Referring now to FIG. 1, a cross-section view of a structure 100 having a first dielectric layer 104 and an analyte-affinity layer 106 is shown, according to an embodiment of the present invention. The first dielectric layer 104 may be composed of any dielectric material known in the art, such as, for example, silicon oxide or silicon nitride. The analyte-affinity layer 106 may be composed any material known to attract a target analyte. For example, the analyte-affinity layer 106 may be composed of gold to attract a target analyte (e.g., a nucleotide sequence or protein).

Figure 2:
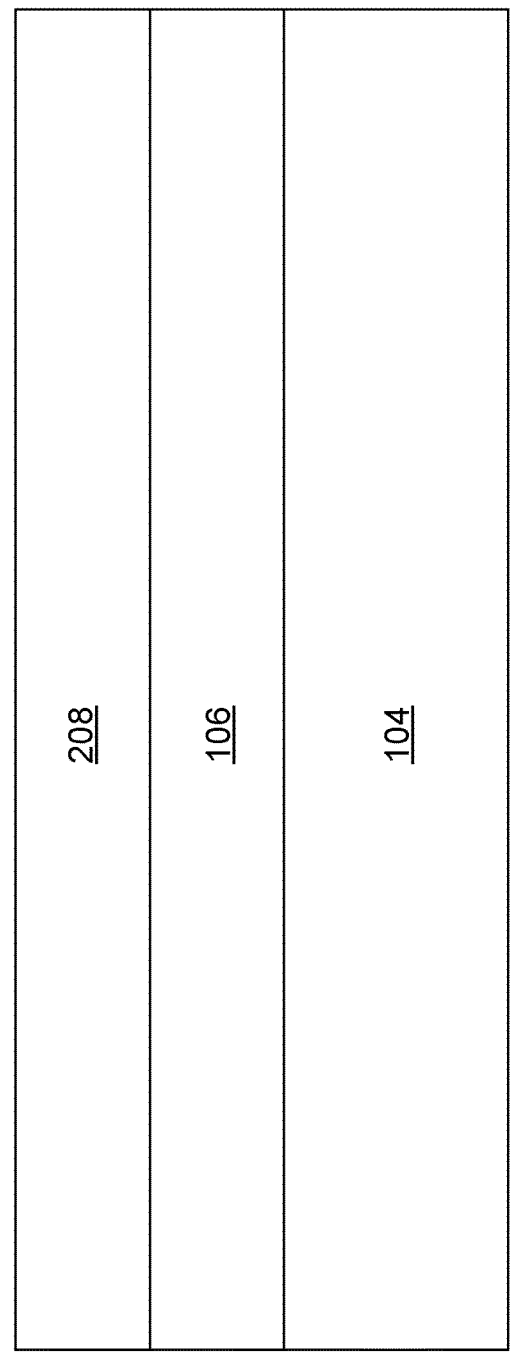
FIG. 2 is a cross-section view of forming a second dielectric layer on the structure, in accordance with an embodiment of the present invention.

Referring now to FIG. 2, a cross-section view of forming a second dielectric layer 208 on the structure is shown, according to an embodiment of the present invention. The second dielectric layer 208 may be formed on an upper surface of the analyte-affinity layer 106. The second dielectric layer 208 may be formed using a conventional deposition technique, such as, for example, atomic layer deposition (ALD), chemical vapor deposition (CVD), physical vapor deposition (PVD), plasma enhanced CVD (PECVD), molecular beam deposition (MBD), pulsed laser deposition (PLD), liquid source misted chemical deposition (LSMCD), or spin on deposition. The second dielectric layer 208 may be composed of any dielectric material known in the art, such as, for example, silicon oxide or silicon nitride. In an embodiment, the second dielectric layer 208 may be composed of a different material than the first dielectric layer 104. For example, if the first dielectric layer 104 is composed of silicon oxide, the second dielectric layer 208 may be composed of silicon nitride.

Figure 3:
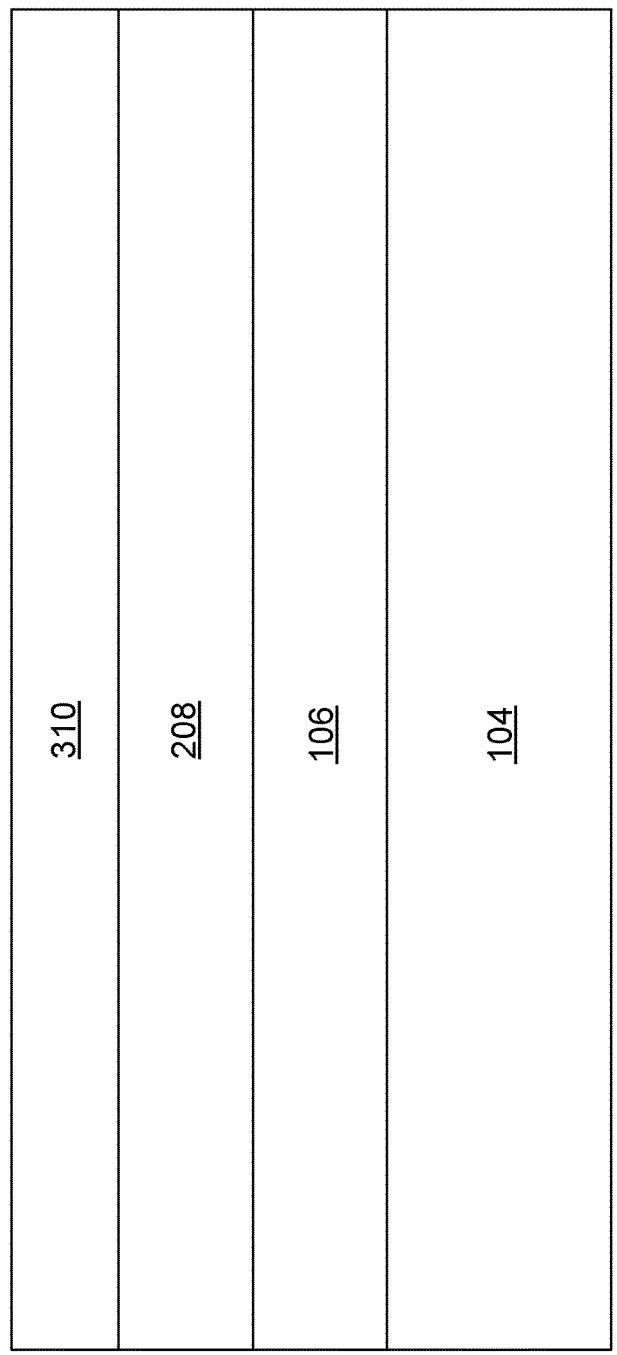
FIG. 3 is a cross-section view of forming a photoresist layer on an upper surface of the second dielectric layer, in accordance with an embodiment of the present invention.

Referring now to FIG. 3, a cross-section view of forming a photoresist layer 310 on an upper surface of the second dielectric layer 208 is shown, according to an embodiment of the present invention. The photoresist layer 310 may be formed using any conventional deposition method, such as, for example, ALD, CVD, PVD, PECVD, MBD, PLD, LSMCD, or spin on deposition. The photoresist layer 310 may be composed of any light-sensitive material known in the art, such as, for example, polymethyl methacrylate (PMMA), polymethyl glutarimide (PMGI), or phenol formaldehyde (PF).

Figure 4:
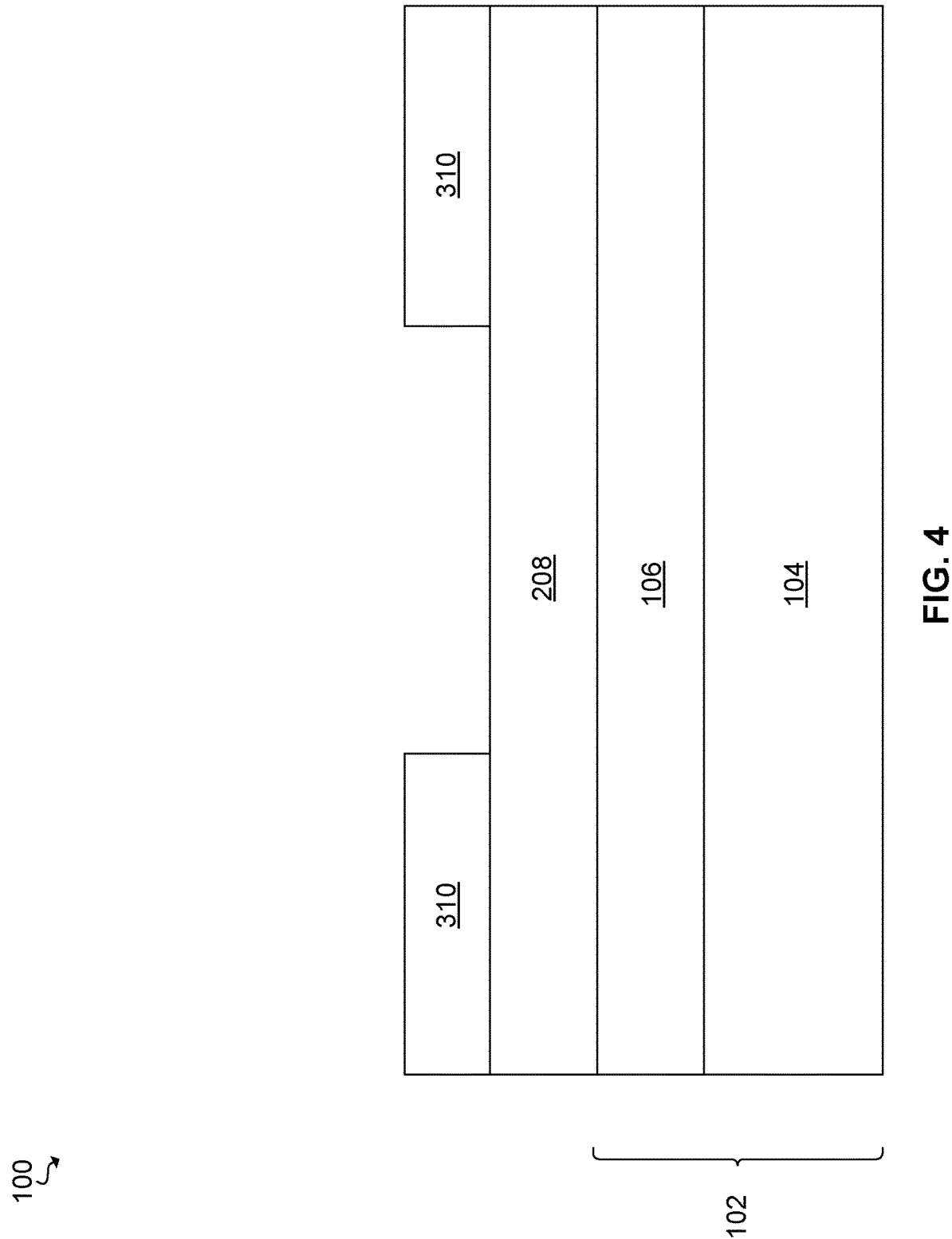
FIG. 4 is a cross-section view of removing a portion of the photoresist layer, in accordance with an embodiment of the present invention.

Referring now to FIG. 4, a cross-section view of removing a portion of the photoresist layer 310 is shown, according to an embodiment of the present invention. The photoresist layer 310 may be removed using any conventional photolithography method, such as, for example, exposure to light and removal by a developer. The portion of the photoresist layer 310 may be removed down to an upper surface of second dielectric layer 208, thus exposing an upper surface of the second dielectric layer 208.

Figure 5:
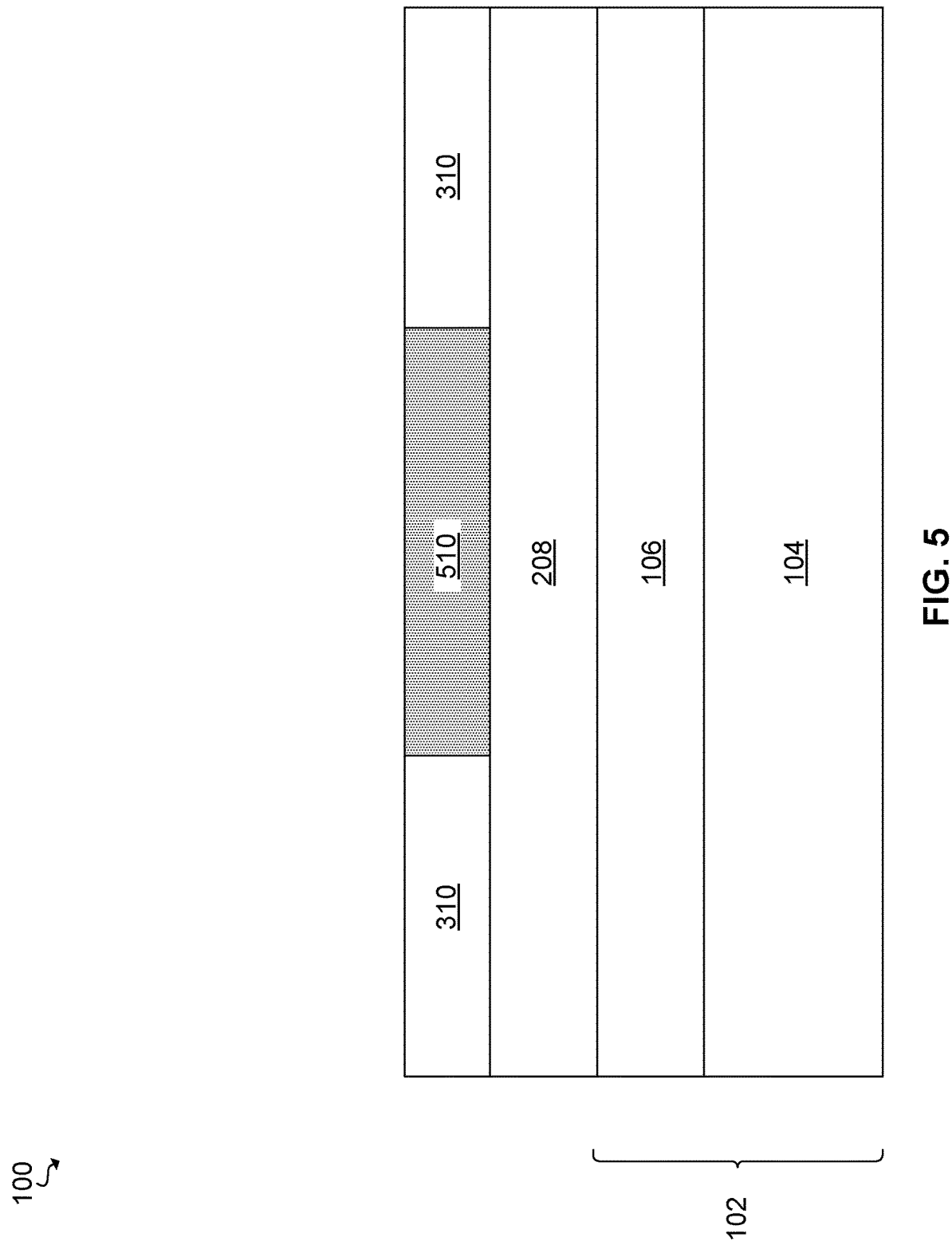
FIG. 5 is a cross-section view of forming a polymer layer on an upper surface of the second dielectric layer, in accordance with an embodiment of the present invention.

Referring now to FIG. 5, a cross-section view of forming a copolymer layer 510 on the exposed upper surface of the second dielectric layer 208 is shown, according to an embodiment of the present invention. The copolymer layer 510 may include a plurality of polymer materials, such as, for example, polyimide and poly(phenylquinoxaline). The copolymer layer 510 may be formed using any deposition method known in the art, such as, for example, PVD or sequential electrospray deposition.

Figure 6:
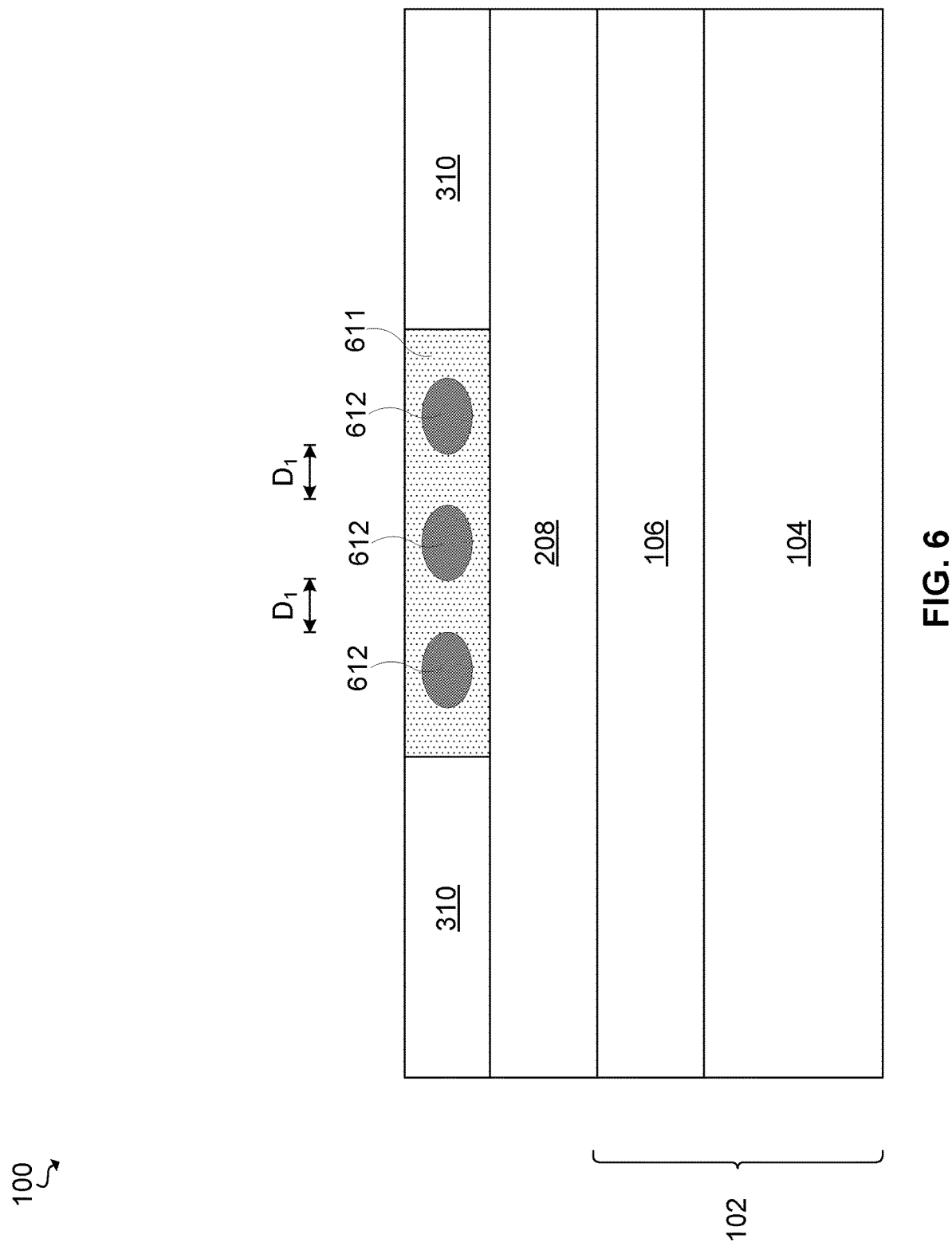
FIG. 6 is a cross-section view of transforming the polymer layer into a first copolymer and a second copolymer, in accordance with an embodiment of the present invention.

Referring now to FIG. 6, a cross-section view of transforming the copolymer layer 510 into a first polymer 612 and a second polymer 611 is shown, according to an embodiment of the present invention. The copolymer layer 510 may be transformed into the first polymer 612 and the second polymer 611 through an annealing process. During the annealing process, polymers having contrasting chemical functionalities may be re-arranged to form a regular periodic pattern of discrete block polymers (e.g., the first polymer 612). At least one first polymer 612 may be formed within the second polymer 611. The first polymer 612 may have an ellipsoid or cylindrical shape. More than one first polymer 612 may be formed within the second polymer 611 where each first polymer 612 may be separated by a distance $D_1$. The distance D1 may be greater than or equal to a length of a target analyte. In an embodiment, if a nucleotide sequence is the target analyte, the distance $D_1$ may range from approximately 50% to approximately 300% of the length of the nucleotide sequence. For example, if a target analyte is a nucleotide sequence having a length of approximately 10 nm (roughly the length of a nucleotide sequence having 50 base pairs), the distance $D_1$ may range from approximately 5 nm to approximately 20 nm. In another example, if a target analyte is a nucleotide sequence having a length of approximately 5 nm (roughly the length of a nucleotide sequence having 25 base pairs), the distance D1 may range from approximately 2.5 nm to approximately 10 nm.

Figure 7A:
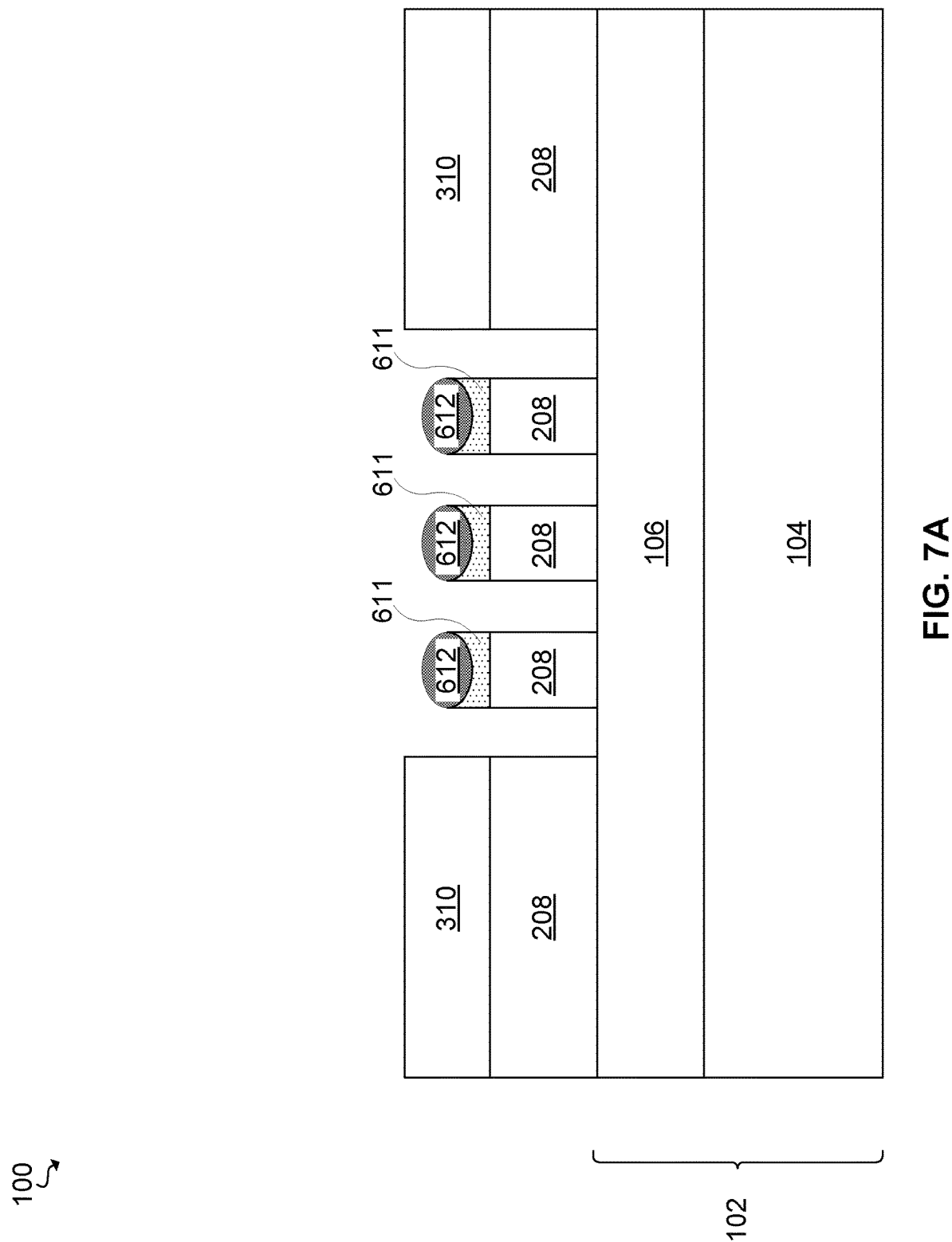
FIGS. 7A-7B are a cross-section view and an isometric view, respectively, of removing a portion of the second copolymer and removing a portion of the second dielectric layer, in accordance with an embodiment of the present invention.
Figure 7B:
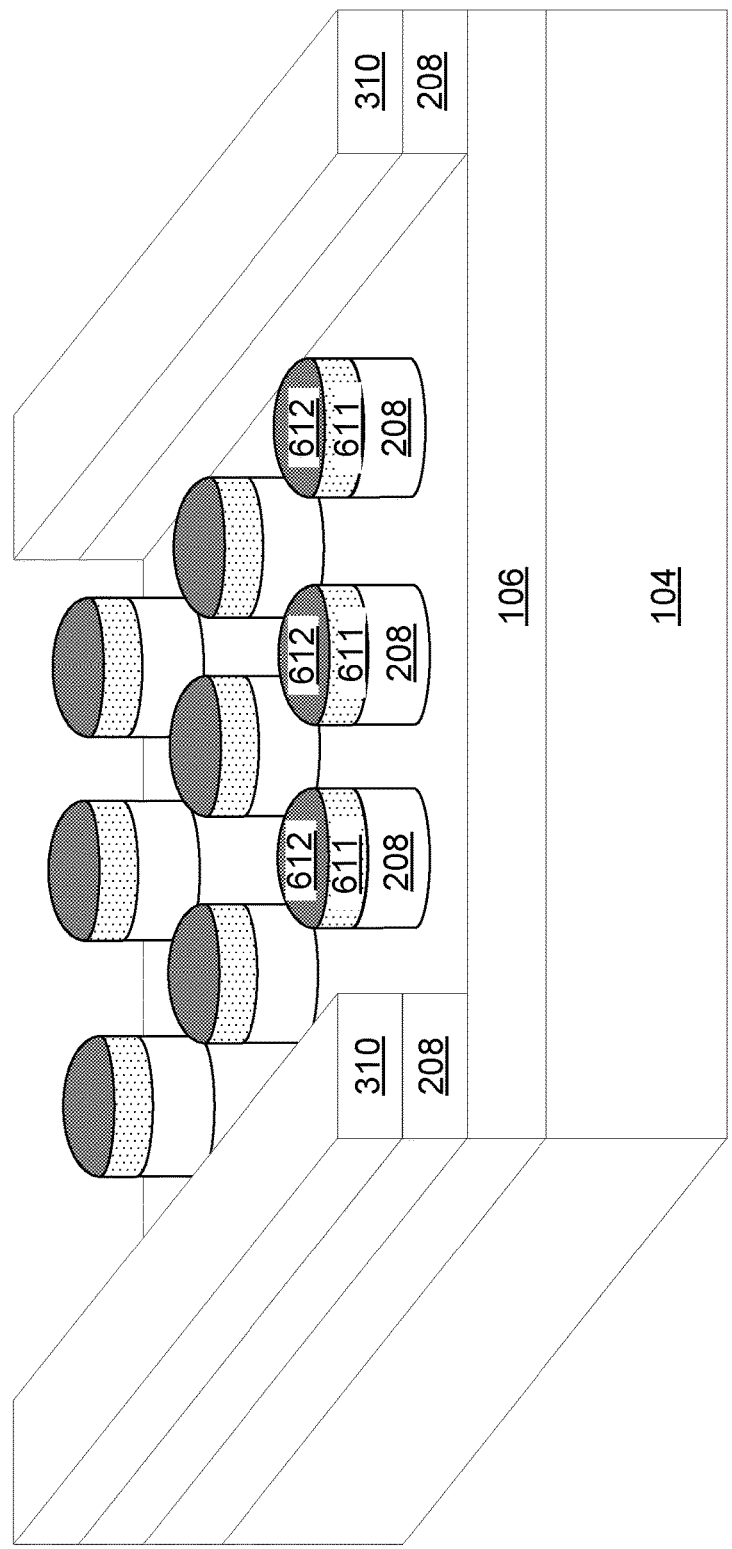

Referring now to FIGS. 7A-7B, a cross-section view and an isometric view, respectively, of removing a portion of the second polymer 611 and removing a portion of the second dielectric layer 208 are shown, according to an embodiment of the present invention. The portion of the second polymer 611 may be removed adjacent to the first polymer 612. In an embodiment, the removed portion of the second polymer 611 may be above and/or a side of first polymer 612. In a preferred embodiment, the removed portion of the second polymer 611 may be above and around an outer circumference of the first polymer 612 such that a second portion of the second polymer 611 remains below the first polymer 612 (as illustrated in FIGS. 7A-7B). The removed portion of the second dielectric layer 208 may be directly below the removed portion of the second polymer 611. The second polymer 611 and the second dielectric layer 208 may be removed by any material removal process known in the art, such as, for example, reactive ion etching (RIE). The material removal process may be selective to the remaining portion of the second polymer 611 and the remaining portion of the second dielectric layer 208 underlying the remaining portion of the second polymer 611. The first polymer 612 and the photoresist layer 310 may prevent material from being removed below the first polymer 612 and the photoresist layer 310, respectively. A portion of the second polymer 611 and a portion of the second dielectric layer 208 may remain below the first polymer 612. The remaining portion of the second dielectric layer 208 may have a cylindrical shape. The remaining portion of the second dielectric layer 208 and the first polymer 611 may have a similar size. For example, a diameter of the second dielectric layer 208 and the first polymer 611 may be within approximately 0 nm and approximately 2 nm of one another.

Figure 8B:
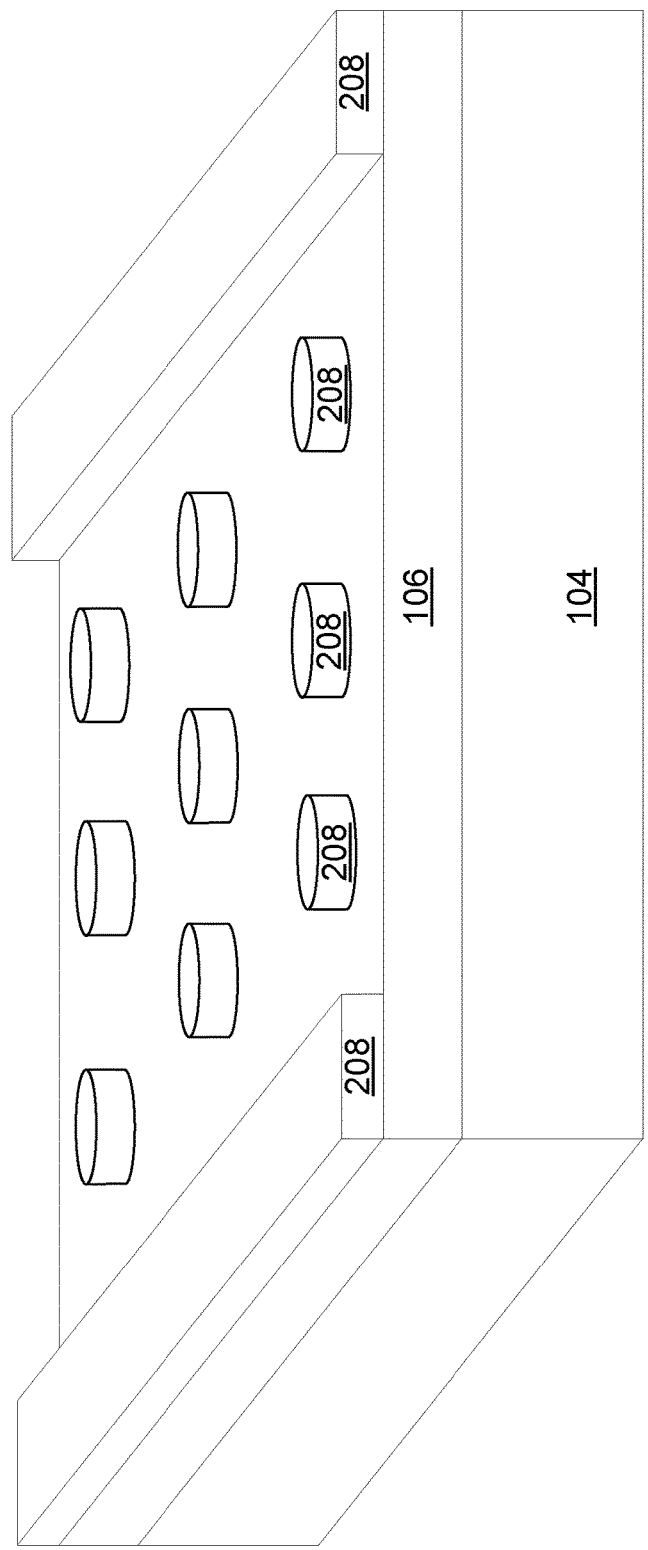

Referring now to FIGS. 8A-8B, a cross-section view and an isometric view, respectively, of removing the first polymer 612, the second polymer 611, and the photoresist layer 310 are shown, according to an embodiment of the present invention. The first polymer 612, the second polymer 611, and the photoresist layer 310 may be removed by any material removal process known in the art, such as, for example, RIE.

Figure 9A:
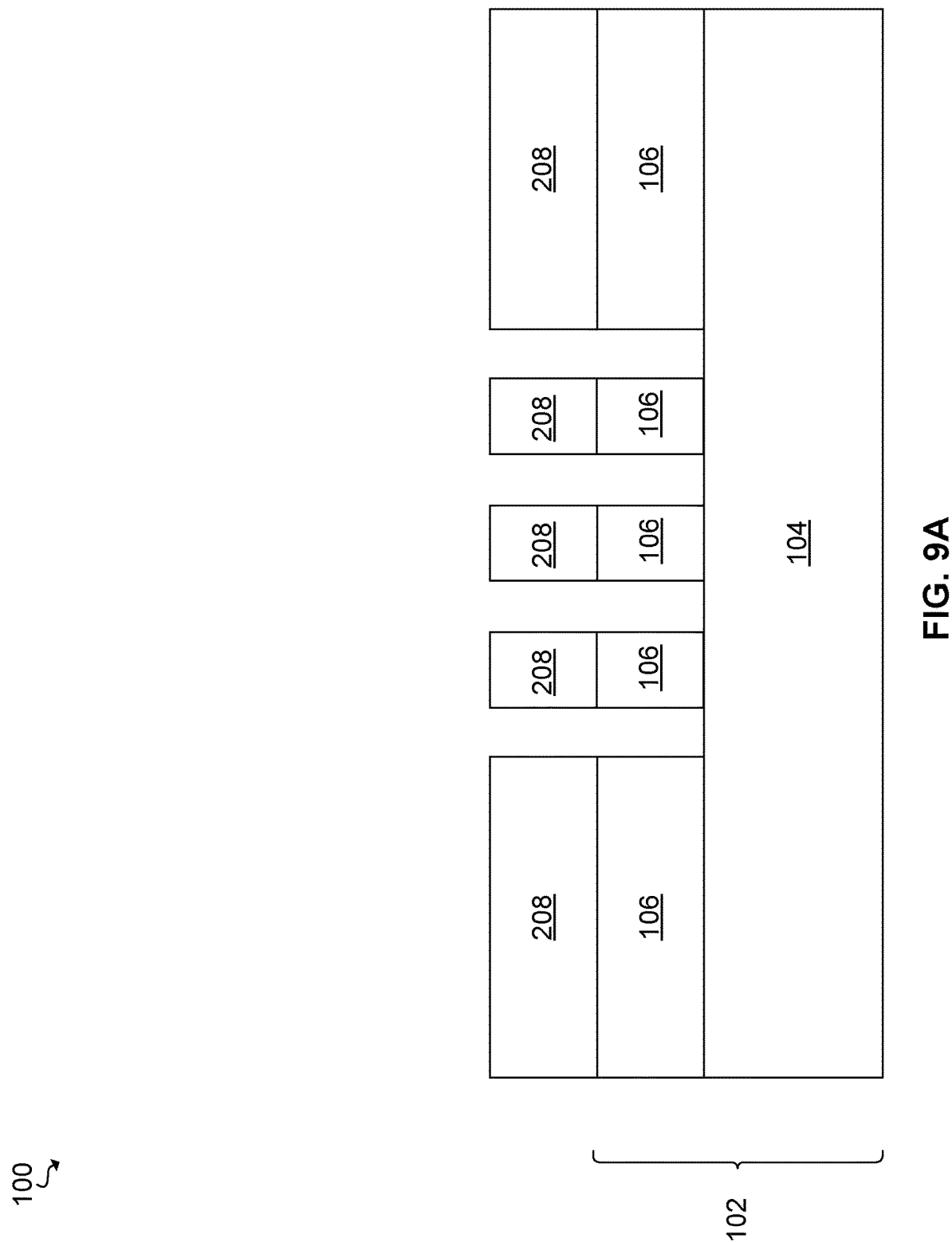
FIGS. 9A-9B are a cross-section view and an isometric view, respectively, of removing a portion of the analyte-affinity layer, in accordance with an embodiment of the present invention.
Figure 9B:
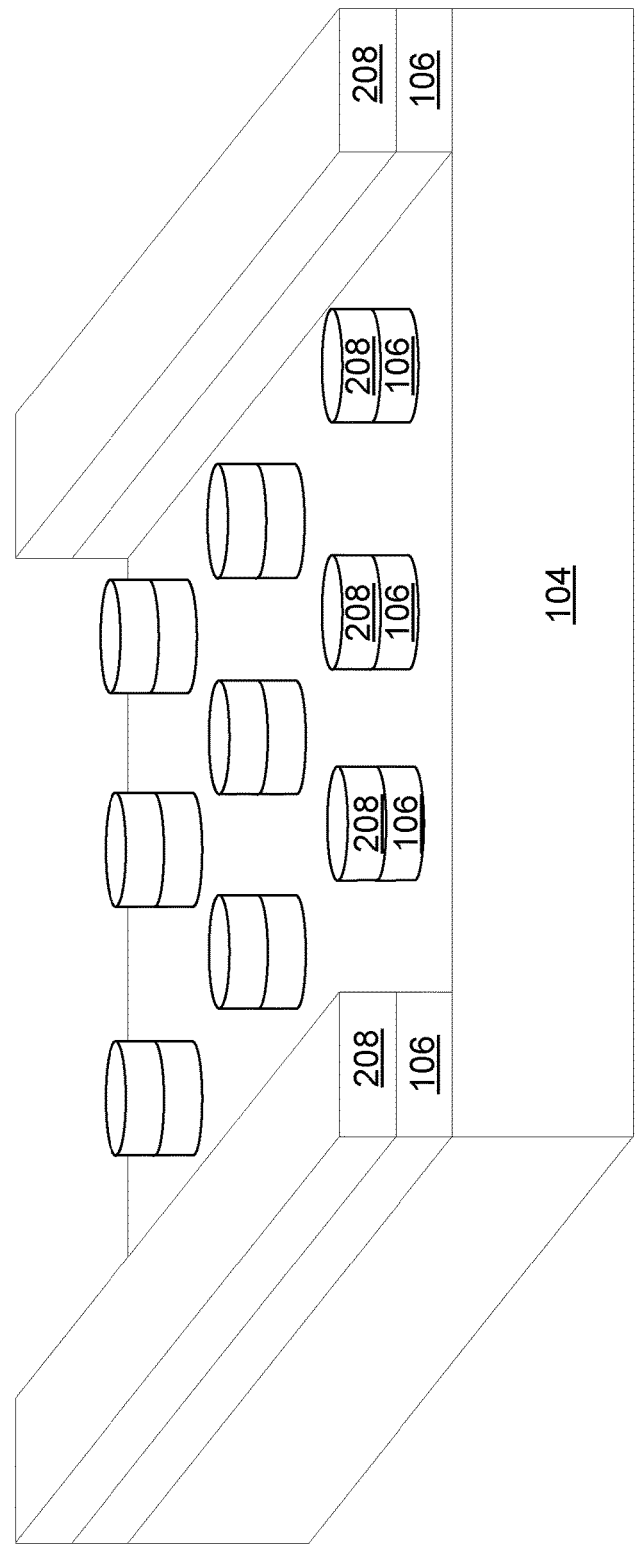

Referring now to FIGS. 9A-9B, a cross-section view and an isometric view, respectively, of removing an exposed portion of the analyte-affinity layer are shown, according to an embodiment of the present invention. The exposed portion of the analyte-affinity layer 106 may not be covered by a remaining portion of the second dielectric layer 208. The exposed portion of the analyte-affinity layer 106 may be removed using any material removal method known in the art, such as, for example, a selective wet etch. An etching process used to remove the exposed portion of the analyte-affinity layer 106 may be selective to the second dielectric layer 208 and the first dielectric layer 104.

Figure 10B:
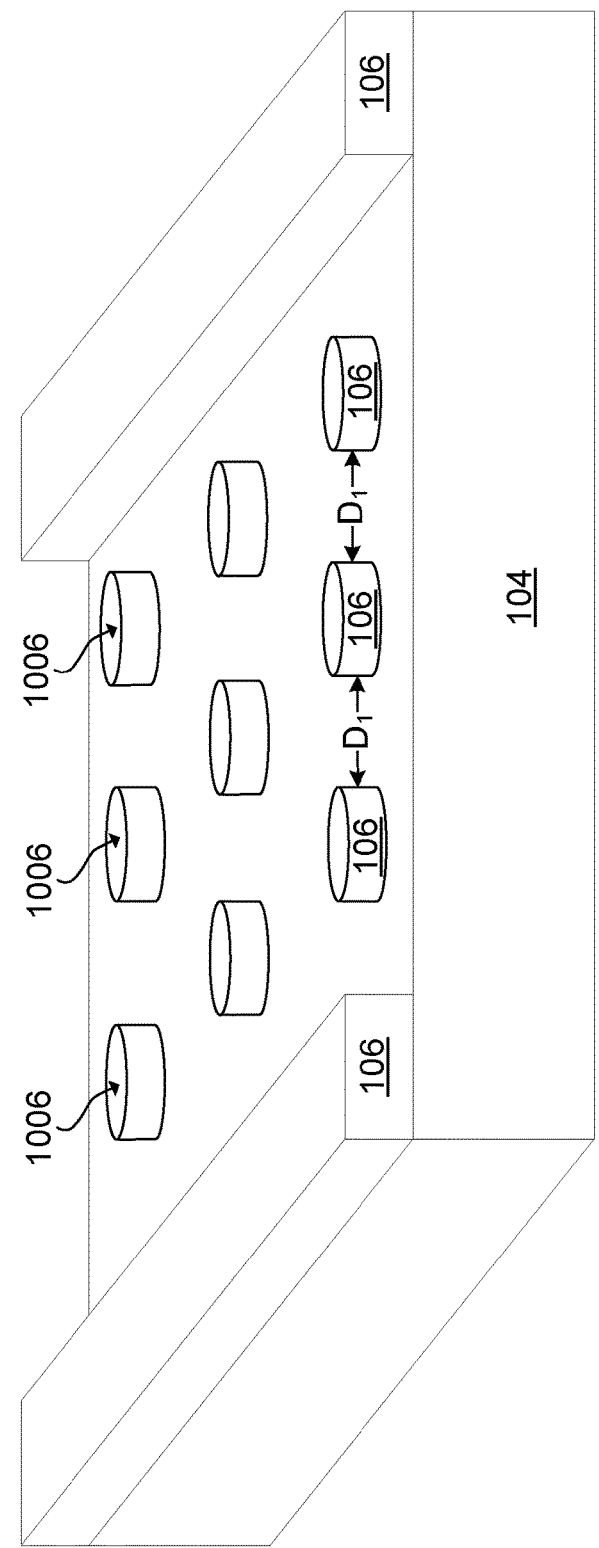

Referring now to FIGS. 10A-10B, a cross-section view and an isometric view, respectively, of removing the second dielectric layer 208 are shown, according to an embodiment of the present invention. The second dielectric layer 208 may be removed using any material removal method known in the art, such as, for example, a selective wet etch. One or more portions of the analyte-affinity layer 106 may remain on an upper surface of the first dielectric layer 104. The one or more remaining portions of the analyte-affinity layer 106 may have a cylindrical shape and an upper surface 1006. In an embodiment, the one or more remaining portions may be separated by at least the distance $D_1$. In another embodiment, the one or more remaining portion may be separated by at least a distance ranging from approximately 0 nm to approximately 2 nm greater or less than the distance $D_1$. In an embodiment, non-cylindrical portions of the analyte-affinity layer 106 may be removed using a conventional material removal process, such as, for example, masking and etching.

Figure 11:
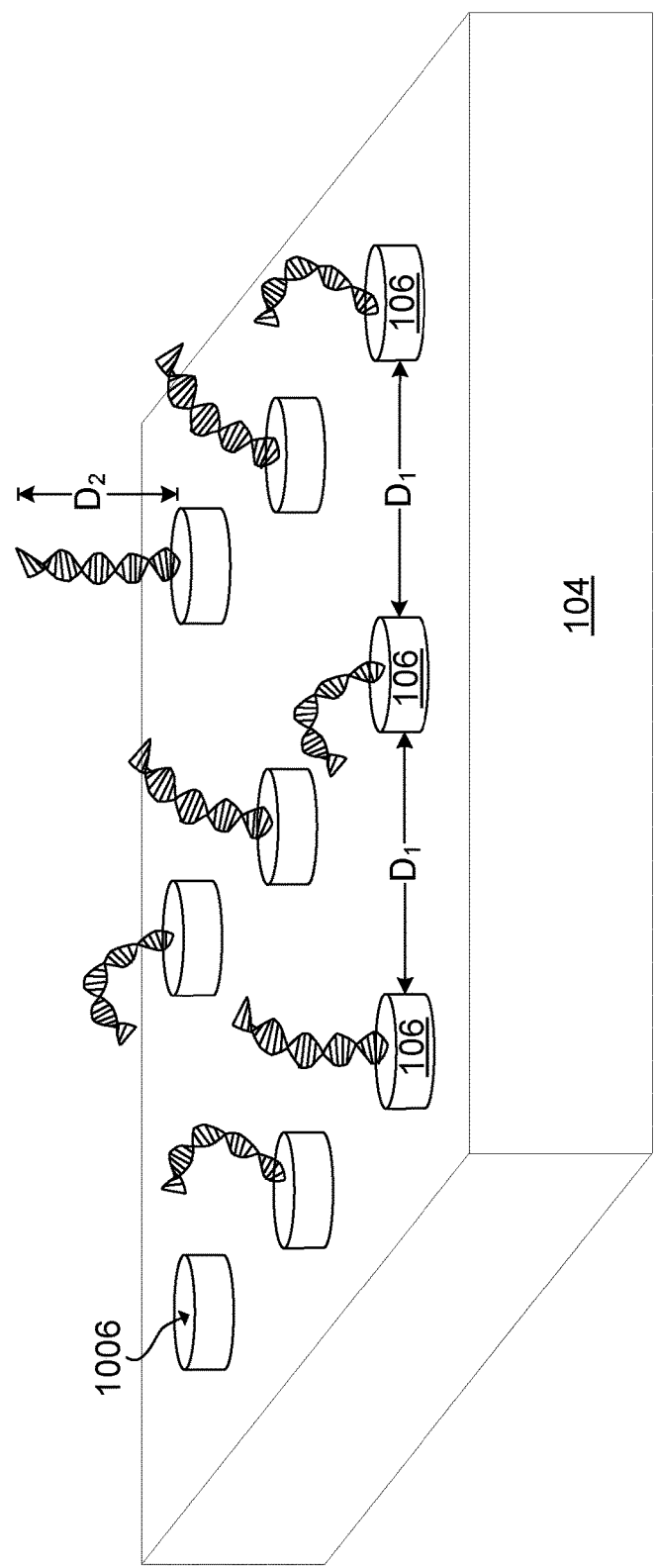
FIG. 11 is an illustration of a biosensor structure, in accordance with an embodiment of the present invention.

Referring now to FIG. 11, a biosensor structure is shown, according to an embodiment of the invention. The biosensor structure may be used to detect one or more target analytes. For example, the biosensor may be used to detect a nucleotide sequence. Remaining cylindrical portion(s) of the analyte affinity layer 106 may attract the nucleotide sequence and/or enable more complete nucleotide hybridization by holding corresponding nucleotide sequences within proximity to one another. An upper surface of the first dielectric layer 104 (e.g., composed of silicon oxide) may repel the nucleotide sequence. Due to a small area of the upper surface 1006 of the remaining cylindrical portion of the analyte-affinity layer 106, only a fully formed pair of nucleotides may stay on the upper surface of the remaining cylindrical portion. For example, the upper surface 1006 of the remaining cylindrical portion of the analyte-affinity layer 106 may have a diameter ranging from approximately 2 nm to approximately 20 nm, and ranges therebetween. For example, the upper surface of the remaining cylindrical portion of the analyte-affinity layer 106 may be approximately 6 nm. A length $D_2$ of a nucleotide sequence may be used to determine a diameter of the upper surface 1006. For example, if a target analyte is a nucleotide sequence having 15 base pairs, the upper surface 1006 may have a diameter ranging from approximately 3 nm to approximately 5 nm. In another example, if a target analyte is a nucleotide sequence having 50 base pairs, the upper surface 1006 may have a diameter ranging from approximately 5 nm to approximately 15 nm.

Since the remaining cylindrical portions may be separated by the distance $D_1$, a target analyte may only adhere to a single cylindrical portion. In addition, the first dielectric layer may be composed of silicon oxide which may repel particular analytes (e.g., a nucleotide sequence). By including isolated analyte-attracting points (e.g., separated gold portions) separated by an analyte repelling region (e.g., an upper surface of the first dielectric layer 104), analyte adhesion to the surface of the biosensor may be more precisely controlled and measured than previously possible with conventional devices. An analyte may be detected on the surface of the biosensor, for example, with an optical sensing device.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method of forming a biosensor having an analyte-affinity layer tailored to reduce false detection of an analyte, the method comprising:

forming a second dielectric layer on an upper surface of a structure, wherein the structure comprises an analyte-affinity layer on a first dielectric layer;

forming a photoresist layer on an upper surface of the second dielectric layer;

removing a portion of the photoresist layer, thereby exposing a portion of the upper surface of the second dielectric layer;

forming a co-polymer layer on the exposed portion of the upper surface of the second dielectric layer;

transforming the co-polymer layer into a first polymer within a second polymer, wherein the transforming comprises forming the first polymer in a regular periodic pattern of discrete block polymers;

removing a first portion of the second polymer adjacent to the first polymer, wherein a second portion of the second polymer remains below the first polymer;

removing a first portion of the second dielectric layer below the first portion of the second polymer down to an upper surface of the analyte-affinity layer, wherein a second portion of the second dielectric layer remains below the first polymer;

removing the first polymer, the second polymer, and the photoresist layer;

removing a first portion of the analyte-affinity layer adjacent to the second portion of the second dielectric layer, wherein a second portion of the analyte-affinity layer remains below the second portion of the second dielectric layer; and removing the second dielectric layer, thereby exposing an upper surface of the second portion of the analyte-affinity layer, wherein steps of removing are performed by any material removal process, steps of forming are performed using a conventional deposition technique, and the step of transforming is performed using an annealing process.

2. The method of claim 1, wherein transforming the copolymer layer into the first polymer within the second polymer includes an annealing process.

3. The method of claim 1, wherein the first polymer is enveloped by the second polymer.

4. The method of claim 1, wherein the first polymer has an ellipsoid shape or a cylindrical shape.

5. The method of claim 1, wherein the second portion of the analyte-affinity layer has a cylindrical shape.

6. The method of claim 1, wherein the upper surface of the second portion of the analyte-affinity layer has a diameter ranging from approximately 3 nm to approximately 20 nm.

7. The method of claim 1, wherein the analyte-affinity layer comprises gold.

8. The method of claim 1, wherein the first dielectric layer comprises silicon oxide.

9. A method of forming a biosensor having an analyte-affinity layer tailored to reduce false detection of an analyte, the method comprising:

forming a second dielectric layer on an upper surface of a structure, wherein the structure comprises an analyte-affinity layer on a first dielectric layer;

forming a photoresist layer on an upper surface of the second dielectric layer;

removing a portion of the photoresist layer, wherein the removing the portion of the photoresist layer exposes a portion of the upper surface of the second dielectric layer;

forming a co-polymer layer on the exposed portion of the upper surface of the second dielectric layer;

transforming the co-polymer layer into a plurality of first polymers within a second polymer, wherein the transforming comprises forming the plurality of first polymers in a regular periodic pattern of discrete block polymers;

removing a first portion of the second polymer adjacent to the first polymer, wherein a plurality of second portions of the second polymer remain below the plurality of first polymers;

removing a first portion of the second dielectric layer below the first portion of the second polymer down to an upper surface of the analyte-affinity layer, wherein the plurality of second portions of the second dielectric layer remain below the plurality of first polymers;

removing the first polymer, the second polymer, and the photoresist layer;

removing a first portion of the analyte-affinity layer adjacent to the plurality of second portions of the second dielectric layer, wherein a plurality of second portions of the analyte-affinity layer remain below the plurality of second portions of the second dielectric layer; and removing the second dielectric layer, thereby exposing an upper surface of the plurality of second portions of the second dielectric layer, wherein steps of removing are performed by any material removal process, steps of forming are performed using a conventional deposition technique, and the step of transforming is performed using an annealing process.

10. The method of claim 9, wherein the transforming includes an annealing process.

11. The method of claim 9, wherein the plurality of first copolymers are enveloped by the second copolymer.

12. The method of claim 9, wherein the plurality of first copolymers have an ellipsoid shape or a cylindrical shape.

13. The method of claim 9, wherein the plurality of second portions of the analyte-affinity layer have a cylindrical shape.

14. The method of claim 9, wherein the plurality of second portions of the analyte-affinity layer have an upper surface with a diameter ranging from approximately 3 nm to approximately 20 nm.

15. The method of claim 9, wherein adjacent portions of the plurality of second portions of the analyte-affinity layer are separated by at least a distance ranging from approximately 50 of a length of a target analyte to approximately 300 of the length of the target analyte.

16. The method of claim 9, wherein the analyte-affinity layer comprises gold.

17. The method of claim 9, wherein the first dielectric layer comprises silicon oxide.

* * * * *